United States Patent
Allen et al.

(10) Patent No.: US 6,280,604 B1
(45) Date of Patent: Aug. 28, 2001

(54) ELECTRODE MATERIALS, SYSTEMS AND METHODS FOR THE ELECTROCHEMICAL DETECTION OF NITRIC OXIDE

(75) Inventors: Barry W. Allen, Durham, NC (US); Louis A. Coury, Lafayette, IN (US); Claude A. Piantadosi, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/523,645

(22) Filed: Mar. 10, 2000

(51) Int. Cl.[7] .................................................. G01N 27/26

(52) U.S. Cl. ................. 205/777.5; 205/778; 205/781; 205/792; 205/793; 204/403; 204/415; 204/291; 600/309; 600/345; 600/353

(58) Field of Search ............................... 205/777.5, 778, 205/781, 792, 793; 204/403, 415, 291; 600/309, 345, 353

(56) References Cited

U.S. PATENT DOCUMENTS

| | | | |
|---|---|---|---|
| 4,158,044 | 6/1979 | Takabatake et al. | 423/235 |
| 4,913,780 | 4/1990 | Habermann et al. | 205/780.5 |
| 5,358,889 | 10/1994 | Emesh et al. | 437/60 |
| 5,409,591 | 4/1995 | Baker et al. | 204/425 |
| 5,466,350 | 11/1995 | Baker et al. | 205/781 |
| 5,565,075 | 10/1996 | Davis et al. | 204/412 |
| 5,603,820 * | 2/1997 | Malinski et al. | 205/781 |
| 5,806,517 * | 9/1998 | Gerhardt et al. | 128/635 |
| 5,980,705 | 11/1999 | Allen et al. | 204/291 |

FOREIGN PATENT DOCUMENTS

| | | |
|---|---|---|
| WO 93/215/18 | 10/1993 | (WO). |
| WO 94/02845 | 2/1994 | (WO). |
| WO 96/16593 | 6/1996 | (WO). |

OTHER PUBLICATIONS

The Chemistry of the Rarer Platinum Metals (Os, Ru, Lr and Rh), W.P. Griffith, Imperial College, London, 1967 Interscience Publishers, a division of John Wiley & Sons, London, New York, Sydney no month available.

Chemically modified electrode for the selective and sensitive determination of nitric oxide (NO) in vitro and in biological systems, F. Pariente, J.L. Also, H.D. Abruna, Department of Chemistry, Baker Labratory, Cornell University, Ithaca, NY 14853–1301, USA.

Preliminary note; The use of gold electrodes in the electrochemical detection of nitric oxide in aqueous solution; Fethi Bedioui, Stephane Trevin and Jacques Devynck; Laboratoire d'Eletrochimie det de Chimie Analytique (URA n° 216 due CNRS), Ecole Nationale Superieure de Chijie de Paris, 11 rue Pierre et Marie Curie 75231, Paris Cedex 05 (France).

Technical Note; An electrochemical microprobe for detecting nitric oxide release in brain tissue; Katsuei Shibuki; Laboratory for Neural Networks, Frontier Research Program, RIKEN, Wako, (Japan).

Pratical nitric oxide measurement employing a nitric oxcide––selective electrode; K. Ichimori, H. Ishida, M. Fukahori, and E. Murakami; Department of Physiology 2, Tokai University, School of Medicine, Bohseidai, Ishara, Kanagawa 259–11, Japan no month/year available.

Nitric Oxide Measurement by Electrochemical Methods; Tadeusz Malinski, Oakland University, Rochester, Michigan, USA; Leszek Czuchajowski; University of Idaho, Moscow, Idaho, USA no month/year available.

Metal Nitrosyls; George B. Richter–Addo; Peter Legzdins; Department of Chemistry; The University of British Columbia; Vancouver, Canada; New York Oxford Press 1992 no month available.

Encyclopedia of Electrochemistry of the Elements; Editor—Allen J. Bard; Department of Chemistry; University of Texas, Austin, Texas; vol. VI; Marcel Dekker, Inc., New York and Basel no month/year available.

Ru and RuO, as Electrical Contact Materials; Preparation and Environmental Interactions; R.G. Vadimsky and R.p. Frankenthal, Bell Laboratories, Murray Hill, New Jersey 07974 and D.E. Thompson, Bell Laboratories, Pisataway, New Jersey 08854 no month/year available.

Spectroscopic and Electrochemical Response to Nitrogen Monoxide of a Cationic Iron Porphyrin Immobilized in Nafion–coated Electrodes of Membranes; Joseph Hayon, Dan Ozer, Judith Rishpon and Armand Bettelheim; Nuclear Research Centre, PO Box 9001, Beer–Sheva 84190, Israel; Department of Biotechnology, Tel–aviv University, Ramat Aviv 69978, Israel no month/year available.

(List continued on next page.)

*Primary Examiner*—Bruce F. Bell
(74) *Attorney, Agent, or Firm*—Nixon & Vanderhye P.C.

(57) ABSTRACT

Nitric oxide-specific electrodes are useful for in situ detection of nitric oxide in biomedical applications and have at least a surface region capable of forming complexes with nitric oxide. The nitric oxide complexes formed at the surface of the electrodes apparently increase the concentration of nitric oxide available for detection, leading to significantly improved relative responses as compared to other known nitric oxide electrode materials. The electrode has at least an exterior surface region which contains ruthenium and/or at least one oxide of ruthenium. The electrodes are pre-conditioned at a potential, or potentials, different than the working potential of the electrode, followed by further conditioning at the working potential. Direct response to nitric oxide has been observed for ruthenium electrodes at or below potentials about +675 mV vs. Ag/AgCl, while ruthenium electrodes paradoxical response to nitric oxide has been observed at potentials above +675 mV vs. Ag/Cl.

68 Claims, 2 Drawing Sheets

Incorporation of Anionic Metalloprorphyrins Into Poly(Pyrrole–Alkylammonium) Films—Part 2. Characterization of the Reactivity of The Iron(III) Porphyrininc–Based Polymer; Fethi Bedioui, Yves Bouhier, Chistian Sorel, Jacques Devynck, Liliane Coche–Guerente, Alain Deronzier and Jean Claude Moutet; Laboratoire d'Electrochimie Analytique et Appliquée (U.R.A. No. 216 du C.N.R.S.), Ecole Nationale Supérieure de chimie de Paris, 11 Rue Pierre et Marie Curie, 75231 Paris Cedex 05, France Laboratoire d'Electrochimie Organique et de Photochimnie Rédox (U.R.A No. 1210 du C.N.R.S.), Univeersité Joseph Fourier, BP 53X, 38041 Grenoble Cedex, France.

A Discussion of Electrochemical Techniques for the Detection of Nitric Oxide; David A. Wink, Danae Christodoulou, May Ho, Murali C. Krishna, John A. Cook, Harold Haut, J. Kemp Randolph, Melani Sullivan, George Coia, Royce Murray, and Thomas Meyer; Chemistry Section, Laboratory of Comparative Carcinogenesis, National Cancer Institute, Frederick Cancer Research and Development Center, Frederick, Maryland 21702; Radiation Biology Section, Radiation Biology Branch, National Cancer Institute, Bethesda Maryland 20892; Medical Systems, Inc., One Plaza Road, Greenvale, New York 11548; and Department of Chemistry, University of North Carolina, Chapel Hill, North Carolina 27514 no month/year available.

The Role of Nickel as Central Metal in Conductive Polymeric Porphyrin Film for Electrocatalytic Oxidation of Nitric Oxide; Aleksander Ciszewski, Eugeniusz Kubaszewski and Marek Loźyński; Institute of Chemistry and Applied Electrochemistry, Poznań University of Technology, PL–60–965 Poznań, Poland.

Electrochemical and spectrophotometric study of the behavior of electropolymerized nickel porphyrin films in the determination of nitric oxide in solution; Stéphane Trevin, Fethi Bedioui, Jacques Devynck; Laboratoire d'Electrochimie et Chimie Analytique (URA No. 216 due CNRS), Ecole Nationale Superirure de chimie de Paris, 11 rue Pierre et Marie Curie, 75231 Paris Cedex 05. France.

Methods in Nitric Oxide Research; Edited by Martin Feelisch; Schwarz, Schwarz Pharma AG, Monheim, Germany and Jonathan S. Stamler, Duke University Medical Center, North Carolina, USA no month/year available.

Electrode Materials for Nitric Oxide Detection; Barry W. Allen (Corresponding Author), Department of Anesthesiology, Duke University Medical Center; Claude A. Piantadosi, Department of Medicine, Duke University Medical Center; Louis A. Coury, Jr., Department of Chemistry, Duke University Medical Center no month/year available.

Electronic Conduction in Oxides; N. Tsuda, K. Nasu, A. Yanase, K. Siratori; Springer–Verlag; Berlin Heidelberg New York London Paris Tokyo Hong Kong Barcelona no month/year available.

Metal Nitrosyls; George B Richter–Addo; Peter Legzdins; Department of Chemistry; The University of British Columbia, Vancouver, Canada; Oxford University Press, 1992 no month available.

Letters of Nature; Nitric oxide release from a single cell measured in situ by a porphyrinic–based microsensor; Tadeusz Malinski & Ziad Taha; Department of Chemistry, Oakland University, Rochester, Michigan 48309–4401, USA no month/year available.

Electrochemical Methods Fundamentals and Applications; Allen J. Bard, Dept. of Chemistry, Univ. of Texas; Larry R. Faulkner, Dept. of Checmistry, Univ. of Illinois no month/year available.

* cited by examiner

*Fig. 3*

ELECTRODE MATERIALS, SYSTEMS AND METHODS FOR THE ELECTROCHEMICAL DETECTION OF NITRIC OXIDE

CROSS-REFERENCE TO RELATED APPLICATIONS

This application is related to copending application Ser. No. 09/399,371, filed Sep. 20, 1999, still pending which in turn is a continuation of application Ser. No. 08/942,354 filed on Oct. 1, 1997 (now U.S. Pat. No. 5,980,705), which in turn is based on, and claims domestic priority benefits under 35 USC § 119(e) from, U.S. Provisional Application Serial No. 60/027,355 filed on Oct. 2, 1996, the entire content of each application and patent being expressly incorporated hereinto by reference.

GOVERNMENT GRANT STATEMENT

This invention was made with Government support under Grant No. 2PO1 HL42444-06 awarded by the National Institutes of Health. The Government has certain rights in the invention.

FIELD OF THE INVENTION

The present invention generally relates to the field of electrochemical detection of nitric oxide and, in preferred embodiments, includes materials for constructing electrodes, microelectrodes, and ultramicroelectrodes (all hereinafter referred to as "electrodes") that exhibit an increased response to nitric oxide after a period of electrochemical conditioning and that chemically increase the concentration of nitric oxide available for detection at the electrode surface and/or catalytically increase the rate constant for the electrolysis of nitric oxide.

In addition, the present invention relates to nitric oxide detector systems that incorporate said nitric oxide electrodes, as well as to the methods herein described for using such detector systems. These systems and methods may be employed usefully to detect nitric oxide in any biological or non-biological liquid sample and/or in any biological system (e.g., near or within a whole organism, tissue, group of cells, individual cell, sub-cellular component, or in any fluid within, bathing or withdrawn from an organism).

BACKGROUND OF THE INVENTION

Nitric oxide (NO.) is a short-lived, free radical gas that has recently been shown to play a fundamental role in biological processes, resulting in a demand for accurate and precise techniques for its detection.

Methods for detecting nitric oxide in biology and medicine include spectrophotometry, chemiluminescence, and paramagnetic resonance. But these techniques generally do not permit rapid measurement at the site of NO. production and therefore are not ideal for following the brief course of production and decay that characterizes the metabolism of nitric oxide in biological samples or systems. Electrochemical detection, however, can follow such transient processes, and several electrodes have been developed for the direct electrochemical detection of nitric oxide.

Recently issued U.S. Pat. No. 5,980,705 (incorporated by reference hereinto) discloses certain novel electrodes and methods for detecting nitric oxide. In general, such electrodes have a surface region formed of a metal which complexes with nitric oxide when exposed to a nitric oxide-containing fluid and exhibit maximal nitric oxide response after being electrochemically conditioned.

SUMMARY OF THE INVENTION

Broadly, the present invention relates to electrodes constructed from materials that exhibit an enhanced response to nitric oxide (after conditioning according to the above-cited U.S. Pat. No. 5,980,705 and/or conditioning and pre-conditioning as described herein) and that may also meet one or more of the following four criteria: 1. form electrically-conducting or electrically-semiconducting oxides (see Example I); 2. exhibit an enhanced response to nitric oxide in the presence of chloride (see Example II); 3. exhibit an enhanced response to nitric oxide after a period of electrochemical pre-conditioning followed by conditioning (see Example III); 4. permit indirect detection of nitric oxide (see Example IV).

The present invention also relates to detector systems that employ, as one or more of their components, the novel nitric oxide electrodes of this invention (see Example V). The detector systems of this invention may usefully detect in vivo, in humans or animals, normal processes or pathological conditions that result in an increase or decrease in nitric oxide production, such as, for example, bacteremia, septicemia, autoimmune diseases, stroke, heart attack, tissue injury, surgical trauma, and vascular penetration (see Example VI).

Most preferably, the electrodes of this invention may be prepared from ruthenium, or have a coating prepared from ruthenium on a core of supporting material. The ruthenium may be combined with one or more other materials as may be desired. Alternatively, electrodes of this invention may be prepared from materials or mixtures of materials other than ruthenium, such that the resulting electrodes exhibit an enhanced response to nitric oxide and also meet one or more of the four criteria listed above. Such materials, in principle, include all metals, metaloids, and non-metals, but most particularly the six metals of the so-called platinum group (elements having atomic numbers 44–46 and 76–78) and the transition group metals, as well as metals, metaloids, and non-metals capable of forming electrically-conducting or electrically-semiconducting oxides, including oxides discussed in Tsuda, N. et al., (1990) Electronic Conduction in Oxides. Berlin: Springer-Verlag, the entire content of which is expressly incorporated hereinto by reference.

BRIEF DESCRIPTION OF THE ACCOMPANYING DRAWINGS

Reference will hereinafter be made to the accompanying drawing FIGURES, wherein.

DETAILED DESCRIPTION OF THE INVENTION

The electrodes of this invention can be incorporated into a broad variety of biomedical and/or clinical medical devices to facilitate biomedical research and to enable the accurate and/or early diagnosis and monitoring of various normal processes, medical conditions and/or disease states in which nitric oxide plays a role. For example, the electrodes of this invention may be incorporated into catheters, needles, cannulas and the like for insertion into a patient or experimental subject (e.g., intravenously, into a synovial capsule (joint capsule), into the cerebrospinal fluid, or through a natural body orifice, such as the urethra). The electrode may thus be brought into proximity to, or contact with, a particular biological fluid, such as blood, urine, synovial fluid and the like to allow for the real time detection in vivo of nitric oxide therein. The electrodes of this invention may therefore be employed usefully for the diagnosis and/or monitoring of bacterial infections (e.g., sepsis), vascular competency, autoimmune diseases (e.g., rheumatoid arthritis) and any other disease or condition in which nitric oxide plays a role. Suffice it to say here that the electrodes of this invention may also be incorporated into patient monitoring equipment (e.g., blood drawing systems) or laboratory bench devices (e.g. blood chemistry analyzers).

The electrode for detecting nitric oxide described herein may thus be fashioned or incorporated into a variety of devices for research in the physical, chemical, biological and medical sciences, as well as for veterinary and medical diagnosis or monitoring. The electrode of this invention is not limited to the size or shape described herein and therefore its configuration may be adapted to virtually any specific end use application. For example, the electrode may be made very small, with a maximum dimension of a few micrometers ($10^{-6}$ meters) or less, for measuring nitric oxide activity in very small fluid samples (e.g. $10^{-6}$ liters or less) in vitro; for insertion, in vivo, between individual living cells in a tissue; or for insertion directly into living cells or subcellular components.

This small size may, for example, be achieved by incorporating the electrode onto a microelectronic device (e.g. on a microchip) or by using abrasion, machining, heat and/or mechanical force to work the electrode material into an appropriate configuration. The electrode material may be electroplated, vapor-deposited, sputtered, printed, silk screened, painted, or otherwise superimposed onto, or incorporated in, an appropriate substrate. The electrode may be encapsulated in glass, an organic polymer, or other material, or it may be unencapsulated.

The electrode may be used invasively in biological research, in veterinary research or diagnosis, and in medical research or diagnosis, by being configured in such a way as to be able to be placed within a living organism, or within living or non-living components thereof, in a location in which nitric oxide activity is to be determined. This may be accomplished by fashioning the electrode into, or incorporating it into, catheters, needles, syringes, surgical or medical instruments, micropipettes, drainage tubes, prostheses, other monitoring devices (such as blood pressure monitors), implants (such as cardiac pacemakers), dialysis apparatus, microdialysis probes, plasmapheresis apparatus, to give but a few examples.

The electrode may be used non-invasively by being fashioned into, or incorporated into, devices for determining nitric oxide activity in samples removed from living organisms. Such sample materials include, but are not limited to, blood, urine, synovial fluid, cerebrospinal fluid, ophthalmic fluids, lymph, extracellular fluid, intracellular fluid, the fluid resulting from organ lavage, surgical drainage fluid, dialysate, cell or tissue cultures or culture media. Such non-invasive devices may be bench-top instruments for use in research or diagnostic laboratories or in bedside instruments for use in clinical or surgical medicine or in field instruments for medical or veterinary practice.

The electrode of this invention may be used to make discrete determinations of nitric acid activity, or may be used for continuous, real-time monitoring or recording of nitric oxide activity.

Electrochemical detector systems for nitric oxide in accordance with the present invention may be embodied in a complete electrode assembly connected to, or incorporated in, an electrochemical instrument (e.g. a potentiostat) in order to permit measurements of nitric oxide in any biological or non-biological liquid sample as well as in a biological system (e.g. in or near a whole organism, a tissue, a group of cells, an individual cell, sub-cellular components, or in any fluid within an organism, bathing organisms or withdrawn from organisms). Preferably, detector systems of this invention include one or more electrodes, a mechanical support for the electrodes, an electrochemical instrument, and electrical conductors to connect the electrode(s) to the electrochemical instrument. At least one of the constituent electrodes is an electrode for detecting nitric oxide of the present invention.

Figures 1A, 1B:
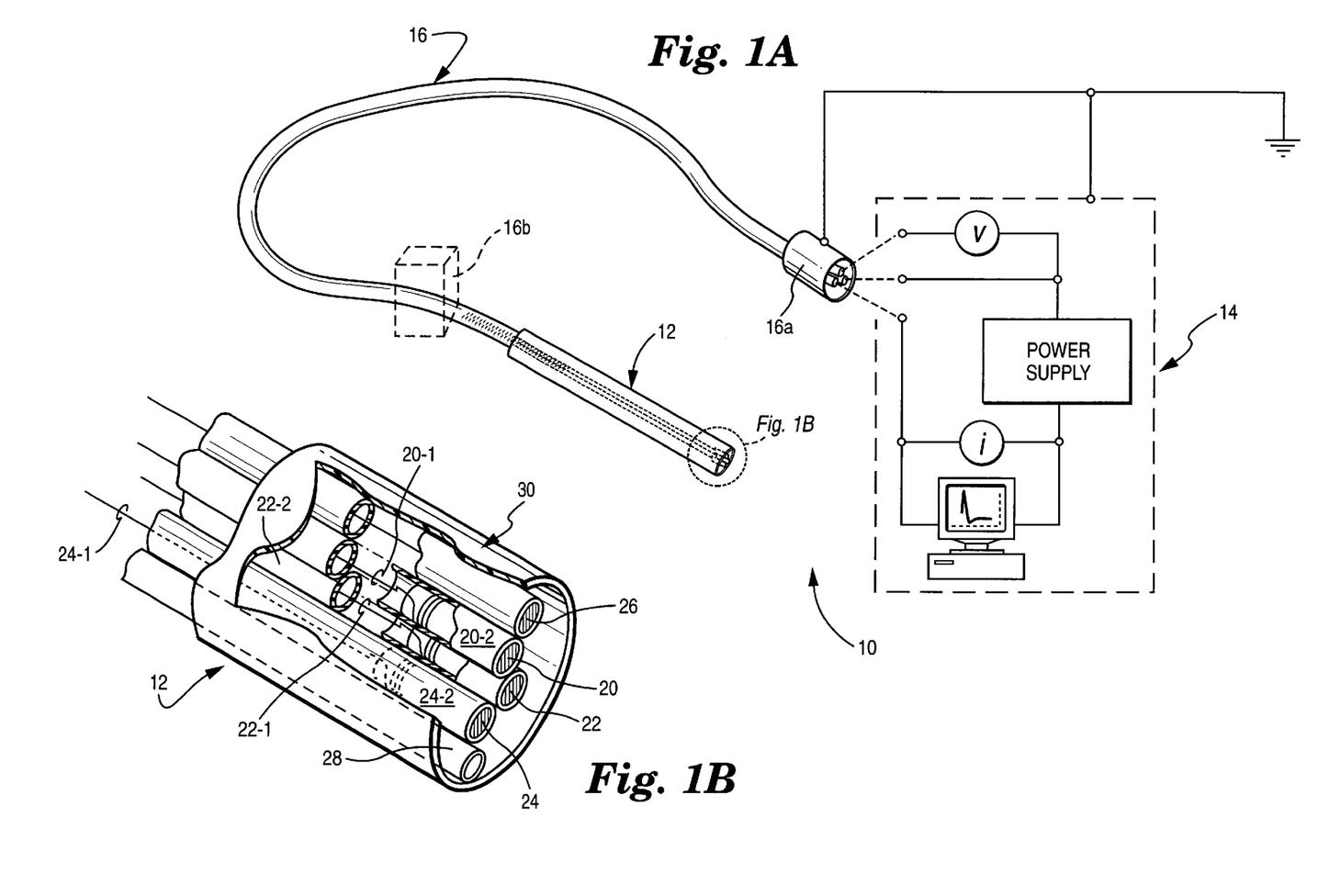
FIG. 1A is a schematic view of an exemplary nitric oxide detector system in accordance with the present invention.
FIG. 1B is an enlarged view of the distal end of the nitric oxide electrode assembly depicted in FIG. 1A.

One exemplary embodiment of a nitric oxide detector system 10 is depicted schematically in accompanying FIG. 1A. As shown therein, the detector system 10 generally includes a distal electrode assembly 12 which is capable of being coupled operatively to a shielded potentiostat 14 via shielded instrument cable 16 and shielded plug 16a. A common connection to ground potential is provided as depicted schematically in FIG. 1A. An optional pre-amplifier (or current multiplier) 16b may be connected in series between the plug 16a and the electrode assembly 12, if needed or desired.

As is perhaps more clearly shown in FIG. 1B, the electrode assembly 12 includes-a nitric oxide electrode 20 (the working electrode), a reference electrode 22, an auxiliary electrode 24, a temperature sensor 26 and an open catheter 28 which provides a pathway for delivery of medication, site irrigation, medical instrument positioning or the like as may be needed and/or desired. The nitric oxide electrode 20 is most preferably conditioned and/or preconditioned and conditioned against the reference electrode and by means of electrical current passed through the auxiliary electrode, if present, in accordance with the techniques described in the above-cited U.S. Pat. No. 5,980,705 or described herein. The individual metal slugs comprising each electrode, which may be formed of the same or different metals, are connected to electrical leads 20-1, 22-1 and 24-1 which extend proximally through the instrument cable 16. Furthermore, an exterior tube 20-2, 22-2 and 24-2 is sleeved over each of the electrodes 22, 24 and 26 and their respective electrical leads 20-1, 22-1 and 24-1 so as to structurally and electrically isolate one from another. An external tube 30 is heat-shrunk around all of the electrodes 20, 22 and 24 as well as the temperature sensor 26 and catheter 28, if present. In this regard, it will be understood that FIGS. 1A and 1B depict such components as being loosely positioned within the external housing tube 30 for ease of reference. In reality, the various components of the probe assembly 12 are tightly retained within the housing tube 30 so as to establish an integral, water-impermeable probe unit.

The detector system 10 and electrode assembly 12 shown in FIGS. 1A and 1B respectively may optionally be provided with additional components as desired to further improve and/or enhance their ability to detect nitric oxide or to adapt them to specific applications. Such additional components may include, for example, multiple working electrodes and/or reference and auxiliary electrodes. A variety of mechanical supports can also be employed, comprising industrial, technical, scientific, or medical tools, instruments or devices (for example a medical cannula, catheter or needle). Further, other devices or techniques, a representative few of which are described below, may be incorporated into the complete sensor to stabilize or enhance the nitric oxide response in the presence of interfering chemical species, in conditions of changing temperature or fluid flow, or in environments in which electrical or electromagnetic noise or mechanical vibration are important factors.

Semi-permeable membranes or coatings may be used to exclude from the sensor chemical species that could be oxidized at the same potential as nitric oxide or otherwise interfere with or block the operation of the nitric oxide sensor.

Methods for compensating for changes in temperature of the fluid to be analyzed for nitric oxide will be employed where such temperature changes would cause a significant change in the nitric oxide oxidation signal.

The rate of any electrochemical reaction generally changes with the rate at which reactants and products are transported to and from the electrode system. Thus, changes in fluid flow could cause a change in the nitric oxide oxidation signal of the present invention that could be misconstrued as a change in nitric oxide activity. This can be minimized or eliminated by reducing the dimensions of the nitric oxide-sensitive electrode (the working electrode) since very small electrodes are less sensitive to changes in fluid flow. The smaller nitric oxide signal resulting from a smaller electrode can be overcome by using a number of very small electrodes in an electrically-coupled array, such that the combined surface areas of all the electrodes approximate the surface area of a single, larger electrode.

Smaller electrodes generally exhibit a higher current densities (current per unit area) than do larger electrodes and therefore can enhance the ratio of signal (electrolysis current in the present invention) to electrical or electromagnetic noise. Therefore for several reasons, instead of a single large electrode, an array of very small electrodes of equivalent total surface area may be used in the complete nitric oxide sensor. The electrodes in such an array must be spaced far enough from each other so that each electrode does not perturb the NO concentration in the vicinity of any of the others.

Ambient electrical or electromagnetic noise permeate electrical conductors and cause extraneous current flow. In cases in which the signals intentionally passed through the conductors are small, such extraneous currents constitute serious interference. Enhancement of the signal-to-noise ratio may be accomplished in the present invention by incorporating an amplifier (or pre-amplifier) at or near the electrodes, to strengthen the signal before it is conducted through the cables that connect to the electrochemical instrument.

Mechanical movement or vibration of electrical conductors can also produce or alter electron flow and is therefore is another source of extraneous current (triboelectric current). Triboelectric currents can be minimized by use of special cables in which the internal conductors are mechanically isolated from the outer sheath of the cable. In addition, pre-amplifiers as well as opto-electric components (in which electrical signals are converted to optical signals and back again to electrical signals) can prevent electrical currents induced in a cable (either electrically or mechanically) from reaching the electrodes of the present invention.

Passive electrical or magnetic shielding can also be used to isolate extraneous electrical currents induced in a cable (either electrically or mechanically) from the complete detector system of the present invention.

A greater understanding of this invention will be gained by the following non-limiting Examples.

EXAMPLE I

Unlike some other metals, ruthenium forms certain electrically-conducting oxides (for example, ruthenium-dioxide, $RuO_2$). For this reason, ruthenium has been used to form contacts in electrical switches in the field of electrical equipment engineering [Vadimski, R. G. and Frankenthal, R. P., (1979) Ru and $RuO_2$ as *Electrical Contact Materials: Preparation and Environmental Interactions.* J. Electrochem Soc.: Solid State Science and Technology, 126(11): p. 2017–2023]. The present inventors found this behavior of certain ruthenium oxides also facilitates the conduction of electrons in a ruthenium electrode, in the field of electrochemical detection of nitric oxide, and may therefore contribute to the enhanced response of the ruthenium electrode to nitric oxide. Other metals, metalloids or non-metals that form electrically conducting or semi-conducting oxides, or mixtures of conductive, semi-conductive and non-conductive oxides, may also prove useful for constructing electrodes for the enhanced detection of nitric oxide.

EXAMPLE II

The chloride ion ($Cl^-$) may be involved in the enhanced response of some nitric oxide electrodes. The role of chloride ($Cl^-$) in the detection of nitric oxide by the electrode of the present invention was investigated as follows.

A ruthenium working electrode was conditioned by being held at a potential of +675 mV vs. Ag/AgCl. for two hours in 7.0 pH phosphate buffer containing 150 mM sodium perchlorate ($NaClO_4$), which does not release chloride, $Cl^-$, in solution. (This was instead of phosphate buffered saline, PBS, containing 150 mM sodium chloride, which does release $Cl^-$ in solution.) However, in order to maintain the same reference potential as in PBS, the Ag/AgCl reference electrode was immersed in PBS behind a water-permeable ceramic frit.

The response of the ruthenium electrode to nitric oxide was greatly diminished in phosphate buffered perchlorate solution (i.e., in the absence of chloride), as compared to the response of the same kind of electrode when exposed to nitric oxide in phosphate buffered saline (i.e., in the presence of chloride). This diminished response of ruthenium was comparable to that of platinum in phosphate buffered saline (i.e., in the presence of chloride, $Cl^-$), and platinum does not show an enhanced response to nitric oxide. These results demonstrate that $Cl^-$ is a factor in the enhanced response of the ruthenium electrode to nitric oxide.

EXAMPLE III

Electrode conditioning in the present invention consists in holding the nitric oxide electrode at a fixed conditioning potential for a period of time sufficient to enhance electrode performance and then, without interruption, continuing to hold the electrode at the same potential while the electrode is exposed to a fluid in which nitric oxide is to be detected. To facilitate an understanding of what follows, it is useful to distinguish the conditioning potential from the working potential, the potential used for detection of nitric oxide, even though they have the same value in the case just described.

A useful variation of the conditioning procedure is accomplished by applying to the electrode a preconditioning potential (or an uninterrupted sequence of such potentials) that may be different from the conditioning potential and/or the working potential.

As noted below, several pre-conditioning profiles were tried, at potentials that were either higher or lower than the working potential, or a combination of both. All of these experiments were performed in chloride-containing buffer, PBS.

Profile A. A ruthenium electrode was pre-conditioned at +200 mV vs. Ag/AgCl for 20 min. after which the potential was immediately stepped up to +675 mV vs. Ag/AgCl (the conditioning potential) and held at that potential for 2 hrs. before the electrode was used for electrochemical measurement at +675 mV (the working potential). The total of pre-conditioning time and conditioning time was, therefore, 2 hours and 20 min.

Profile B. A ruthenium electrode was pre-conditioned at +800 mV vs. Ag/AgCl for 20 min. after which the potential was immediately stepped down to +675 mV vs. Ag/AgCl and held at that potential for 2 hrs. before the electrode was used for electrochemical measurement at +675 mV. The total of pre-conditioning time and conditioning time was again 2 hours and 20 min.

Profile C. A ruthenium electrode was pre-conditioned by continuously alternating +200 mV vs. Ag/AgCl with +800 mV vs. Ag/AgCl at 2 Hz. for 40 min. prior to conditioning at +675 mV vs. Ag/AgCl for 2 hrs. The total of pre-conditioning time and conditioning time was 2 hours and 40 min.

After profile A, the electrochemical response of ruthenium to nitric oxide was consistently increased to the highest levels that had previously been attained by conditioning the electrode solely at the working potential.

After profile B, the electrochemical response of ruthenium to nitric oxide was increased to higher levels than seen in profile A, but electrode performance was not as consistent as with Profile A, and the oxidation signal exhibited greater electrical noise.

After profile C, the electrochemical response of ruthenium to nitric was consistently increased to higher levels than with pre-conditioning Profile A and the signal was electrically quiet.

For ruthenium, at least, pre-conditioning profiles A and C appear to be superior to pre-conditioning profile B. Pre-conditioning Profile A has the further advantage that it can be implemented with simpler electrochemical instruments (potentiostats) that allow only manual adjustment of the potential applied to the electrode. Other pre-conditioning profiles may be used and are not limited to the three profiles described above. Also three or more pre-conditioning potentials may prove useful. These or other pre-conditioning profiles may enhance the ability of materials other than Ru to serve as electrodes for the detection of nitric oxide, including other metals, metaloids and non-metals.

EXAMPLE IV

Figures 2A, 2B, 3:
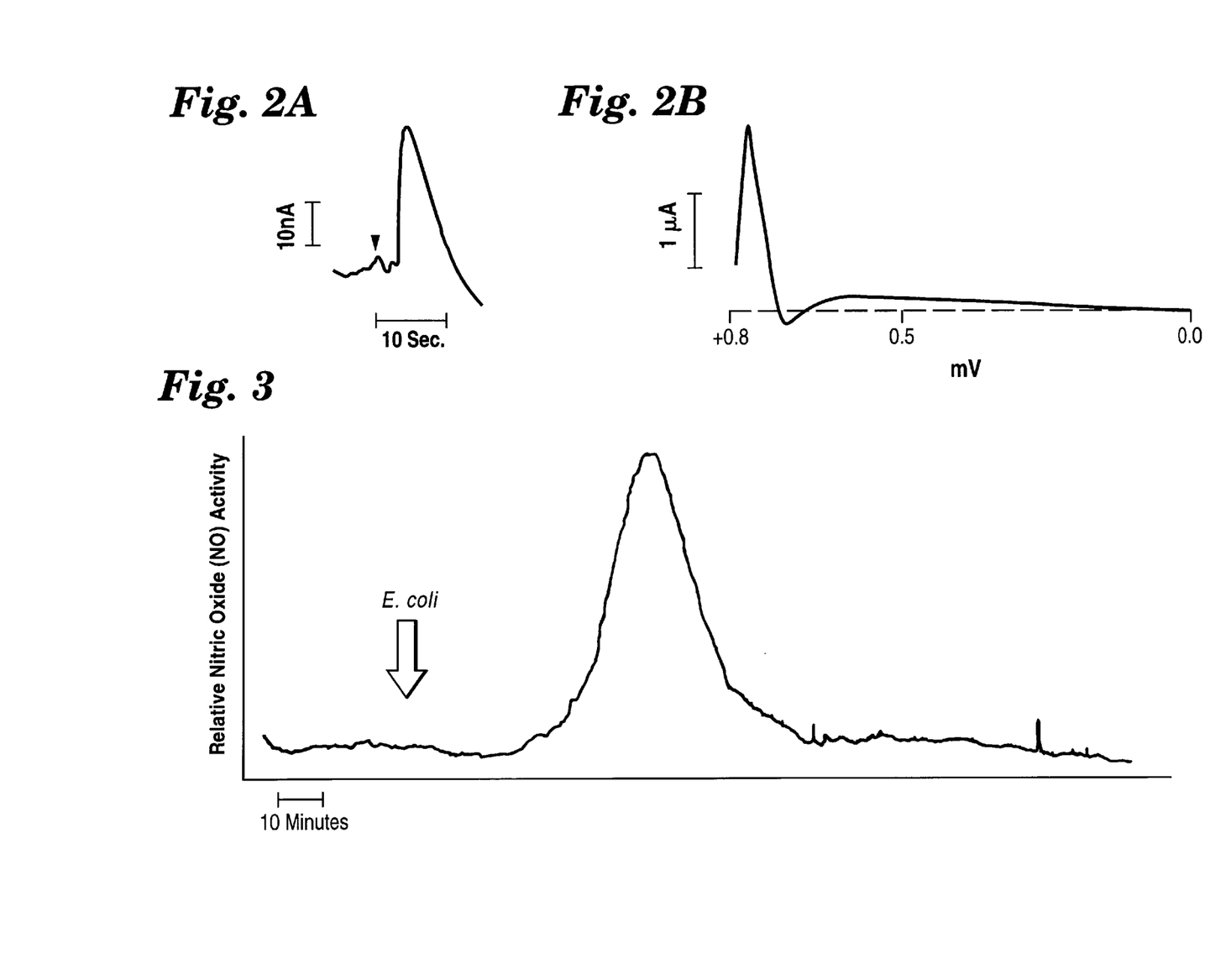
FIG. 2A is an amperogram showing the indirect response of a ruthenium electrode observed according to Example IV.
FIG. 2B is a plot of the computed difference current between two linear voltametric scans performed, respectively, in the presence and absence of nitric oxide according to Example IV.
FIG. 3 is a graphical plot of relative nitric oxide activity versus time for the in vivo experiment conducted according to Example VI below.

At fixed potentials above +675 mV vs. Ag/AgCl, the behavior of the ruthenium electrode changed dramatically: the current response to nitric oxide exhibited two peaks instead of one, and the second peak was very large and, paradoxically, in the unexpected direction. Specifically, at a fixed potential of +800 mV vs. Ag/AgCl, an injection of 1.5 $\mu$M NO. into PBS produces the expected downward current peak, consistent with a flow of electrons towards the working electrode, an oxidation. This initial peak was immediately followed by a large upward-going current peak that was not expected. Both peaks are shown in the amperogram of FIG. 2A. The present inventors term the expected downward response the direct response to nitric oxide, since it could arise from the oxidation of nitric oxide without the intervention of any other chemical processes; and they term the upward peak the indirect response, since it could not arise directly from an oxidation or a reduction of nitric oxide.

This upward-going response could also be seen in a plot of the computed difference current between linear voltametric scans performed, respectively, in the presence and absence of NO. as evidenced in FIG. 2B. More specifically, the plot of FIG. 2B represents the difference between two linear scan voltagrams, one performed in PBS saturated with 1.5 $\mu$M NO. and one performed in PBS saturated with $N_2$. As is evident therein, a large upward peak is present between about +700 and +800 mV, vs. Ag/AgCl.

Although the indirect response appeared consistent with an electrochemical reduction, there was no known component of the analyte buffer employed in this example that would be reduced at the high positive potentials used here. (Nitric oxide is reduced at negative potentials.) While not wishing to be bound to any particular theory at this time, the present inventors believe that the indirect response is likely due to the suppression of the oxidative background current (presumably chloride oxidation or the electrolysis of water) after a film forms on the electrode surface consisting essentially of nitrosyl-ruthenium complexes or nitrosyl-chlororuthenium complexes (or structural isomers thereof). Such a film could decrease the rate of oxidation of $Cl^-$ or $OH^-$. The resulting indirect signal is many times larger than the oxidation signal, and could be used to detect NO., but has a slow time course.

The strong response of the ruthenium electrode to the direct oxidation of NO. may be useful in sensors for biomedical applications. The even stronger indirect (paradoxical) response may be useful in applications in which a rapid response is not as important.

EXAMPLE V

A complete electrode assembly, according to the present invention, was constructed similarly to that shown in FIGS. 1A and 1B as follows. A few turns of a forty-centimeter length of 30 gauge copper wire were wrapped tightly around one end of a solid cylindrical slug of ruthenium metal that was 1 cm. long and 0.5 mm in diameter; the remaining length of the wire extended from the slug to form an electrical lead. This process was repeated for similar slugs of silver and platinum. Each slug was then inserted, along with its electrical lead wire, into a separate, expanded tube of the fluoropolymer FEP such that the slugs were completely enclosed in the tubes, but 10 centimeters of the copper wire protruded from one end of each tube. The triad of ruthenium, silver, and platinum slugs, lead wires and FEP tubes was then inserted into a single, larger expanded FEP tube so that the three slugs were completely enclosed in the larger tube, aligned with each other, and the three electrical leads protruded from one end of the large FEP tube. This assembly was heated at a moderate temperature to shrink the FEP around the slugs and leads. (See the schematic representation thereof depicted in accompanying FIG. 1B.)

The electrode assembly was electrically shielded and then enclosed in another expanded FEP tube, with lead wires and shielding protruding at one end. Moderate heat was again applied to shrink the FEP. The conductors of a shielded, three-conductor instrument cable were then electrically connected to the protruding wires and electrode shielding, and the other end of the cable was terminated with a shielded plug. The electrode assembly and its junction with the cable were inserted into an expanded tube of a different fluoropolymer, PTFE. Intense heat was then applied to shrink the outer layer of expanded PTFE and to fuse all inner layers of FEP, resulting in a tightly encapsulated sensor and cable assembly. The encapsulant was trimmed to expose the tips of the slugs, and the sensor tip was then polished abrasively, cleaned, and dried.

The sensor tip was then exposed to hexamethyl-disilazane and dried in an oven. Reaction with silazane provides a hydrophobic surface that excludes water from the microscopic spaces between the metal slugs and the encapsulant. The sensor tip was again repolished, cleaned and dried to remove the hydrophobic coating only from the exposed surfaces of the metal disk electrodes. The sensor tip was immersed in Nafion™ (Dupont), an anion-exclusion coating, then dried again. The tip of the finished electrode was hydrated in phosphate buffered saline prior to being used for detecting nitric oxide. Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements associated with the spirit and scope of the appended claims. For example, one or more catheter lumens may be incorporated into the sensor assembly.

EXAMPLE VI

A complete detector system as described in Example V, above, was used to detect nitric oxide in vivo, according to an experimental animal protocol approved by the National Institutes of Health. Specifically, an adult male baboon (*Papio cynocephius*) was anesthetized and ventilated mechanically. An intravascular nitric oxide sensor was inserted in a femoral vein. The working electrode was pre-conditioned at +200 mV (vs. Ag/AgCl) for 20 minutes and then conditioned at +675 mV (vs. Ag/AgCl) for two hours. Later, heat killed bacteria (*E. coli*) were infused into a brachial vein. Approximately twenty minutes later, the output of the nitric oxide detector system, as shown in accompanying FIG. 3, demonstrated a strong oxidation signal (shown in the upward direction here for graphical purposes to signify an increase in nitric oxide), consistent with the production of nitric oxide by the animal in response to the experimental bacteremia. Other in vivo experiments, using laboratory rats, with an approved protocol, showed similar responses by the nitric oxide detector system after infusion of lipopolysacharide (LPS), a component of bacteria. This response was confirmed as a true nitric oxide response, since it was abolished by injection of an inhibitor of biological nitric oxide production (L-nitroarginine methyl ester) thirty minutes prior to infusion of LPS.

These experiments demonstrate use of the nitric oxide detector system of the present invention to give early warning of bacteremia. This sensor could be incorporated on the tip of a standard medical catheter (or other invasive device) to diagnose, or monitor therapy for, bacteremia or other pathological conditions that result in nitric oxide production. Such conditions include, for example, bacteremia, septicemia, auto-immune diseases, stroke, heart attack, tissue injury, surgical trauma, and vascular penetration.

The nitric oxide electrode assembly can take any form needed for a specific application, since metal can be deposited on supporting substrates using a variety of methods, including micro-photolithography, sputtering, chemical vapor deposition, electroplating, screen printing, etc. Thus, the nitric oxide sensor could be deployed in a linear fashion, as a stripe, band or helix on a medical catheter. Such a linear or curvilinear nitric oxide sensor could detect nitric oxide production in the tissues along the route of catheter penetration, providing early warning of infection reaching the patient from the catheter itself. A contaminated catheter, or other medical device, thus detected could be removed before systemic infection became established.

Alternatively, a non-invasive nitric oxide detector system constructed according to the present invention includes an electrode assembly and sample chamber enclosed within, or in proximity to, the housing of the electrochemical instrument, with provision for the introduction into the sample chamber of discrete fluid samples in which nitric oxide activity is to be determined. Such samples could, for example, be blood, or any other body fluid, withdrawn from an experimental subject or a clinical or veterinary patient. Such a detector system, would also be useful for determining nitric oxide activity in non-biological samples.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An electrode for detecting nitric-oxide having a surface region formed of a material which, at an electrochemical working potential thereof, complexes with nitric oxide when exposed to a nitric oxide-containing fluid, and which exhibits maximal nitric oxide response after being held, prior to nitric oxide exposure, at a pre-conditioning potential different from the working potential thereof, followed by subsequent conditioning at the working potential thereof.

2. The electrode of claim 1, wherein the material is at least one selected from the group consisting of metals, metaloids, electrically-conducting or electrically semiconducting oxides, and mixtures thereof.

3. The electrode of claim 1, wherein the electrode does not exhibit a maximal response to nitric oxide after being conditioned at its working potential, but does exhibit a maximal response to nitric oxide after being conditioned at both said pre-conditioning potential and said working potential.

4. The electrode of claim 1, wherein the pre-conditioning potential is greater than the working potential thereof.

5. The electrode of claim 1, wherein the pre-conditioning potential is less than the working potential thereof.

6. The electrode of claim 1, wherein the pre-conditioning potential is alternately changed between a first potential which is less than the working potential thereof, and a second potential which is greater than the working potential thereof.

7. The electrode subjected to a preconditioning potential according to one or more preconditioning profiles as in any one of claims 4–6.

8. A method for the in vivo detection of nitric oxide comprising placing an electrode according to any one of claims 1–6 at a site within a patient or other living organism, and then determining the nitric oxide present at said site by the electrochemical response of said electrode.

9. The method of claims 8, wherein said step of determining the nitric oxide present at said site includes subjecting the electrode to a predetermined fixed potential which causes said electrode to electrochemically respond directly to the presence of nitric oxide at said site.

10. The method of claim 9, wherein said predetermined fixed potential is less than about +675 mV vs. Ag/AgCl.

11. The method of claim 8, wherein said step of determining the nitric oxide present in said sample includes subjecting the electrode to a predetermined fixed potential which causes said electrode to electrochemically respond indirectly to the presence of nitric oxide at said site.

12. The method of claim 11, wherein said predetermined fixed potential is greater than about +675 mV vs. Ag/AgCl.

13. The method of claim 8, wherein said step of determining the presence of nitric oxide at said site includes subjecting the electrode to a fixed potential sufficient to suppress oxidative background current.

14. The method of claim 13, wherein said background current is suppressed by allowing a film consisting essentially of nitrosyl complexes or any structural isomers thereof to form on said electrode surface.

15. A method of detecting nitric oxide in a biological sample comprising bringing an electrode according to any one of claims 1–6 into contact with the biological sample, and then determining the nitric oxide present in said sample by the electrochemical response of said electrode.

16. The method of claim 15, wherein said step of determining the nitric oxide present in said sample includes subjecting the electrode to a predetermined fixed potential which causes said electrode to electrochemically respond directly to the presence of nitric oxide in said sample.

17. The method of claim 16, wherein said predetermined fixed potential is less than about +675 mV vs. Ag/AgCl.

18. The method of claim 15, wherein said step of determining the nitric oxide present in said sample includes subjecting the electrode to a predetermined fixed potential which causes said electrode to electrochemically respond indirectly to the presence of nitric oxide in said sample.

19. The method of claim 18, wherein said predetermined fixed potential is greater than about +675 mV vs. Ag/AgCl.

20. The method of claim 15, wherein said step of determining the presence of nitric oxide at said site includes subjecting the electrode to a fixed potential sufficient to suppress oxidative background current.

21. The method of claim 20, wherein said background current is suppressed by allowing a film consisting essentially of nitrosyl complexes (or any structural isomers thereof) to form on said electrode surface.

22. The electrode of claim 1, wherein said complex is a nitrosyl complex or any structural isomer thereof.

23. The electrode of claim 1, wherein at least the surface region consists essentially of ruthenium and/or at least one oxide of ruthenium.

24. The electrode of claim 1, wherein at least the surface region includes at least one oxide of ruthenium having the formula $RuO_x$, where x is a number greater than 0.

25. The electrode of claim 24, wherein x is a number greater than 0 up to and including about 2.

26. The electrode of claim 1, wherein the electrode response to nitric oxide is enhanced by the presence of a chloride-containing species on said electrode surface region thereof.

27. The electrode of claim 1, wherein the electrode response to nitric oxide is enhanced by the formation on the electrode surface region of an electrically-conductive oxide.

28. The electrode of claim 1, wherein the elctrode is comprised of ruthenium and/or at least one oxide of ruthenium.

29. An electrode for the detection of nitric oxide in a biological sample having a surface region formed of a material which, at an electrochemical working potential thereof, complexes with nitric oxide when exposed to a nitric oxide-containing fluid, and which exhibits maximal nitric oxide response after being held, prior to nitric oxide exposure, at a pre-conditioning potential different from the working potential thereof, followed by subsequent conditioning at the working potential thereof.

30. The electrode of claim 29, wherein the material is at least one selected from the group consisting of metals, metaloids, electrically-conducting or electrically semiconducting oxides, and mixtures thereof.

31. The electrode of claim 29, wherein the electrode does not exhibit a maximal response to nitric oxide after being conditioned at its working potential, but does exhibit a maximal response to nitric oxide after being held at both said pre-conditioning potential and said working potential.

32. The electrode of claim 29, wherein the pre-conditioning potential is greater than the working potential thereof.

33. The electrode of claim 29, wherein the pre-conditioning potential is less than the working potential thereof.

34. The electrode of claim 29, wherein the pre-conditioning potential is alternately changed between a first potential which is less than the working potential thereof, and a second potential which is greater than the working potential thereof.

35. The electrode subjected to a preconditioning potential according to one or more preconditioning profiles as in any one of claims 32–34.

36. The electrode of claim 29, wherein said complex is a nitrosyl complex or any structural isomer thereof.

37. The electrode of claim 29, wherein at least the surface region consists essentially of ruthenium and/or at least one oxide of ruthenium.

38. The electrode of claim 37, wherein at least the surface region includes at least one oxide of ruthenium having the formula $RuO_x$, where x is a number greater than 0.

39. The electrode of claim 38, wherein x is a number greater than 0 up to and including about 2.

40. The electrode of claim 29, wherein the electrode is comprised of ruthenium and/or at least one oxide of ruthenium.

41. A method of making an electrode for the detection of nitric oxide having a surface region formed of a material which, at an electrochemical working potential thereof, complexes with nitric oxide when exposed to a nitric oxide-containing fluid, which method comprises conditioning at least the surface region of the electrode by (i) subjecting the surface region to one or more pre-conditioning potential(s) different from the working potential, and then subsequently (ii) subjecting the surface region to conditioning at the working potential.

42. The method of claim 41, wherein the material is at least one selected from the group consisting of metals, metaloids, electrically-conducting or electrically semiconducting oxides, and mixtures thereof.

43. The method of claim 41, wherein the pre-conditioning potential is greater than the working potential thereof.

44. The method of claim 41, wherein the pre-conditioning potential is less than the working potential thereof.

45. The method of claim 41, wherein the pre-conditioning potential is alternately changed between a first potential which is less than the working potential thereof, and a second potential which is greater than the working potential thereof.

46. A method of making an electrode which comprises subjecting the electrode to a preconditioning potential according to one or more preconditioning profiles as in any one of claims 43–45.

47. An electrode for the detection of nitric oxide made according to any one of claims 41–45.

48. A nitric oxide detector system comprising an electrode having a surface region formed of a material which complexes with nitric oxide when exposed to a nitric oxide-containing fluid, a mechanical support for the electrode, and electrical conductors to electrically connect the electrode to an electrochemical instrument.

49. The system of claim 48, wherein the material is at least one selected from the group consisting of metals, metalloids, electrically-conducting or electrically semiconducting oxides, and mixtures thereof.

50. The system of claim 48 or 49, comprising plural electrodes, at least one of which has a surface region formed of said material which complexes with nitric oxide when exposed to a nitric oxide-containing fluid.

51. The system of claim 50, wherein said mechanical support includes a support tube sleeved over said plural electrodes.

52. The system of claim 51, further comprising a temperature probe adjacent to said plural electrodes.

53. The system of claim 50, further comprising a catheter adjacent to said plural electrodes.

54. The system of claim 50 wherein said support tube is sleeved over said plural electrodes, said temperature probe and said catheter.

55. A nitric oxide detector system comprising a probe assembly which includes a plurality of individual electrodes, at least one of which is formed of a material which complexes with nitric oxide in response to contact with a nitric oxide-containing fluid and generates a signal in response thereto, an electrochemical instrument which receives said signal and outputs a signal indicative of nitric oxide presence in said fluid, and instrument cabling which operatively connects the individual electrodes to said electrochemical instrument.

56. The system of claim 55, wherein the material is at least one selected from the group consisting of metals, metalloids, electrically-conducting or electrically semiconducting oxides, and mixtures thereof.

57. The system of claim 48 or 55, wherein said at least one electrode has a surface region formed of said material which, at an electrochemical working potential thereof, complexes with nitric oxide when exposed to a nitric oxide-containing fluid, and which exhibits maximal nitric oxide response after being held, prior to nitric oxide exposure, at a pre-conditioning potential different from the working potential thereof, followed by subsequent conditioning at the working potential thereof.

58. The system of claim 57, wherein the electrode does not exhibit a maximal response to nitric oxide after being conditioned at its working potential, but does exhibit a maximal response to nitric oxide after being conditioned at both said pre-conditioning potential and said working potential.

59. The system of claim 57, wherein the pre-conditioning potential is greater than the working potential thereof.

60. The system of claim 57, wherein the pre-conditioning potential is less than the working potential thereof.

61. The system of claim 57, wherein the pre-conditioning potential is alternately changed between a first potential which is less than the working potential thereof, and a second potential which is greater than the working potential thereof.

62. A method of detecting a pathological condition which produces or suppresses nitric oxide comprising bringing an electrode which complexes with nitric oxide into nitric oxide detecting proximity of a biological sample, measuring nitric oxide present in the sample, whereby a pathological condition which produces or suppresses nitric oxide can be determined.

63. The method of claim 62, wherein said electrode has a surface region formed of a material which, at an electrochemical working potential thereof, complexes with nitric oxide when exposed to a nitric oxide-containing fluid, and which exhibits maximal nitric oxide response after being held, prior to nitric oxide exposure, at a pre-conditioning potential different from the working potential thereof, followed by subsequent conditioning at the working potential thereof.

64. The method of claim 62 or 63, wherein the material is at least one selected from the group consisting of metals, metalloids, electrically-conducting or electrically semiconducting oxides, and mixtures thereof.

65. The method of claim 64, wherein the electrode does not exhibit a maximal response to nitric oxide after being conditioned at its working potential, but does exhibit a maximal response to nitric oxide after being conditioned at both said pre-conditioning potential and said working potential.

66. The method of claim 62 or 63, wherein the pre-conditioning potential is greater than the working potential thereof.

67. The method of claim 62 or 63, wherein the pre-conditioning potential is less than the working potential thereof.

68. The method of claim 62 or 63, wherein the pre-conditioning potential is alternately changed between a first potential which is less than the working potential thereof, and a second potential which is greater than the working potential thereof.

* * * * *